: US011513045B2

United States Patent
Harris et al.

(10) Patent No.: US 11,513,045 B2
(45) Date of Patent: Nov. 29, 2022

(54) TENSION TESTING APPARATUS

(71) Applicant: Intelligent Concrete, LLC, Elbert, CO (US)

(72) Inventors: David W. Harris, Elizabeth, CO (US); Jonathan S. Belkowitz, Elbert, CO (US)

(73) Assignee: Intelligent Concrete, LLC, Elbert, CO (US)

(*) Notice: Subject to any disclaimer, the term of this patent is extended or adjusted under 35 U.S.C. 154(b) by 359 days.

(21) Appl. No.: 16/360,548

(22) Filed: Mar. 21, 2019

(65) Prior Publication Data
US 2020/0300738 A1    Sep. 24, 2020

(51) Int. Cl.
*G01N 3/08* (2006.01)
*G01N 3/04* (2006.01)

(52) U.S. Cl.
CPC .............. *G01N 3/08* (2013.01); *G01N 3/04* (2013.01); *G01N 2203/0016* (2013.01); *G01N 2203/0266* (2013.01)

(58) Field of Classification Search
CPC .. G01N 3/24; G01N 3/04; G01N 3/08; G01N 2203/0016; G01N 2203/0266; F16G 13/06
USPC .......................................................... 73/826
See application file for complete search history.

(56) References Cited

U.S. PATENT DOCUMENTS

| | | | | |
|---|---|---|---|---|
| 2,125,116 A | * | 7/1938 | Lewis | G01N 3/10 73/798 |
| 2,534,980 A | * | 12/1950 | Lubahn | G01N 3/18 374/49 |
| 2,669,868 A | * | 2/1954 | Shneider | G01N 3/10 73/837 |
| 6,026,692 A | * | 2/2000 | Brovold | B29C 43/04 73/818 |
| 6,681,640 B2 | * | 1/2004 | Canumalla | G01N 3/04 73/856 |
| 6,718,833 B2 | * | 4/2004 | Xie | G01N 3/32 73/789 |
| 2020/0103322 A1 | * | 4/2020 | Regimand | G01N 3/04 |

* cited by examiner

*Primary Examiner* — Octavia Hollington
(74) *Attorney, Agent, or Firm* — Foley & Lardner LLP

(57) ABSTRACT

A tension testing apparatus and system is disclosed in which the tension testing apparatus includes a first box including a first outer plate and a first inner plate, a second box including a second outer plate and a second inner plate, and a test sample holding system coupled to the first inner plate and the second inner plate. The first outer plate and the first inner plate may be coupled together by at least two rods. The second outer plate and the second inner plate may be coupled together by at least two other rods. The test sample holding system may be configured to hold a test sample. The at least two rods of the first box may be configured to pass through the second inner plate. The at least two rods of the second box may be configured to pass through the first inner plate.

15 Claims, 7 Drawing Sheets

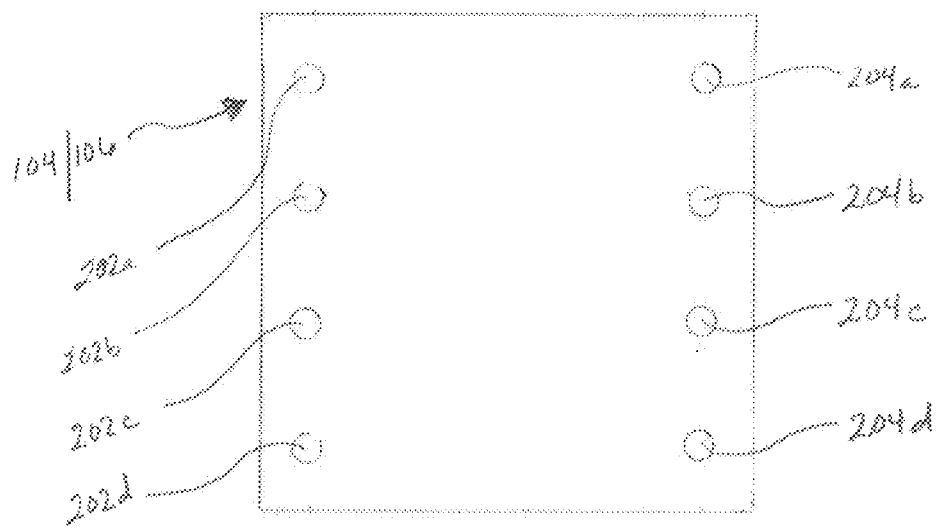
FIG. 2A
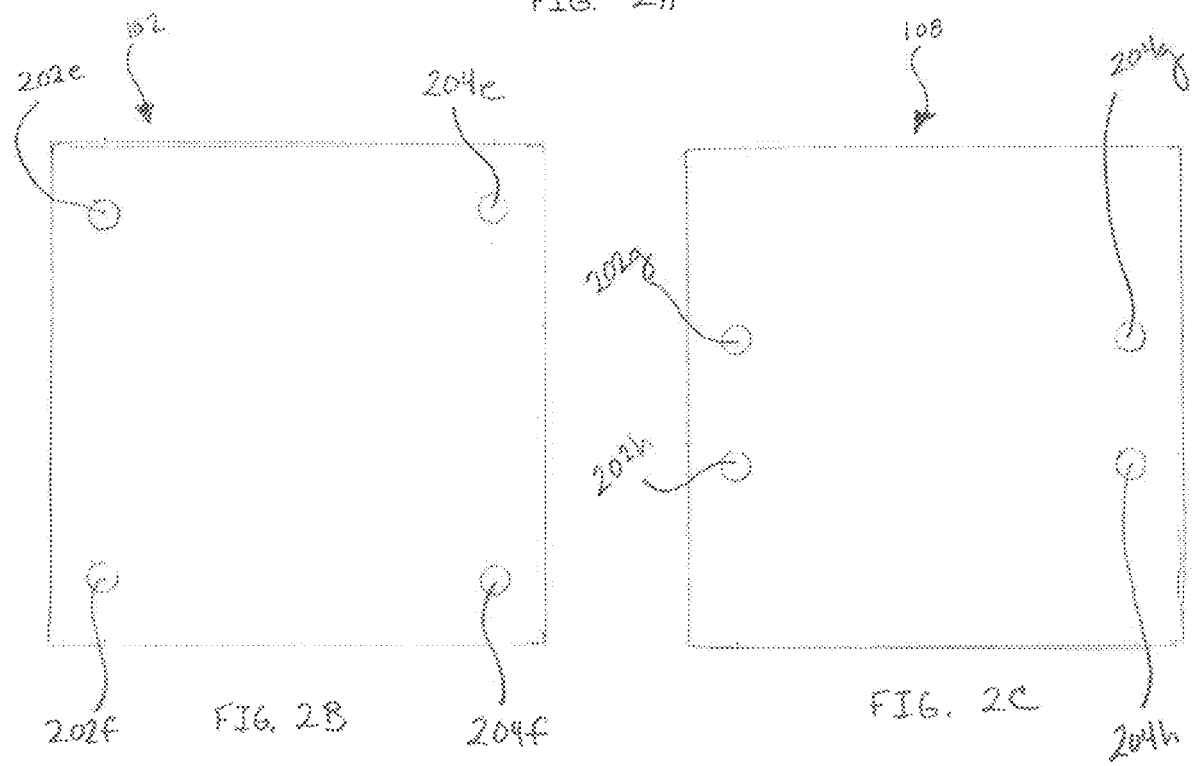
FIG. 2B
FIG. 2C

TENSION TESTING APPARATUS

BACKGROUND

Concrete has been an important part of developing civilizations for thousands of years as one of the oldest construction materials. Concrete is a versatile material that can be used for a variety of construction projects. For certain projects, the strength of the concrete must be tested to determine whether the concrete is suitable for the particular construction project.

Typically, to determine the strength of concrete, the compression strength and/or the tension strength of the concrete is measured. A conventional compression strength test may be the ASTM-C39/C39M-15a Standard Test Method for Compressive Strength of Cylindrical Concrete Specimens. This test uses a uniform compression load applied to a concrete cylinder with the strength being measured as the failure stress or the maximum load from the test divided by the area of the cylinder. However, testing the tension strength of concrete is not as straightforward.

One commonly used test, ASTM C496/C496M-11 Standard Test Method for Splitting Tensile Strength of Cylindrical Concrete Specimens, relies on a test configuration that places a bar along the length of the cylinder and causes a failure approximately across the diameter of the cylinder. Calculating the splitting tensile strength from the test configuration relies on using a theoretical equation derived from structural mechanics, which is wrought with assumptions. Unfortunately, the values calculated from this equation are well known to be significantly greater than the values calculated for a cylinder tested in direct tension.

Another standard test, C78/C78M-15a Standard Test Method for Flexural Strength of Concrete (Using Simple Beam with Third-Point Loading), places a concrete beam in bending. By using this test, the flexural strength, i.e., the strength at failure, is calculated using a theoretical equation from the elastic behavior of the concrete beam in bending; however, assumptions must be made to perform the flexural strength calculation. Moreover, the values obtained from this calculation are also well known to be greater than direct tension values.

Some limited access laboratories, such as the U.S. Bureau of Reclamation Laboratory, have testing machines that can perform direct tension testing. However, these testing machines can cost upwards of $500,000, thereby making a capital investment in such machines cost prohibitive. A straightforward direct tension method and apparatus for testing concrete is not readily available.

SUMMARY

The present disclosure generally relates to concrete testing methods and a concrete testing apparatus, and more particularly, to a tension testing apparatus.

In one or more scenarios, the disclosed technology relates to a tension testing apparatus including a first box comprising a first outer plate and a first inner plate, in which the first outer plate and the first inner plate are coupled together by at least two rods; a second box comprising a second outer plate and a second inner plate, in which the second outer plate and the second inner plate are coupled together by at least two other rods; and a test sample holding system coupled to the first inner plate and the second inner plate, in which the test sample holding system are configured to hold a test sample. In one or more scenarios, the at least two rods of the first box are configured to pass through the second inner plate, and the at least two rods of the second box are configured to pass through the first inner plate.

In one or more scenarios, the disclosed technology relates to a tension testing system including a testing machine configured to apply compression force to a test sample, in which the testing machine includes a moving head and a fixed head; and a tension testing apparatus configured to be positioned within the testing machine. In one or more scenarios, the tension testing apparatus includes a first box comprising a first outer plate and a first inner plate, in which the first outer plate and the first inner plate are coupled together by at least two rods, a second box including a second outer plate and a second inner plate, in which the second outer plate and the second inner plate are coupled together by at least two other rods, and a test sample holding system coupled to the first inner plate and the second inner plate, in which the test sample holding system is configured to hold a test sample.

By way of overview, in one or more scenarios, the tension testing apparatus 100 includes two boxes constructed with plates and rods, in which the first box includes a first outer plate 108 and an inner plate 104 and the second box includes a second outer plate 102 and an inner plate 106. The two boxes provide tension in the test sample while applying a compressive load. The second outer plate 102 and the first outer plate 108 may contact on the testing machine platens. In one or more scenarios, the second outer plate 102 and the first outer plate 108 may include one or more threaded connections each configured to receive a steel rods, thereby allowing the surface of the second outer plate 102 and/or the first outer plate 108 to smoothly contact the testing machine platens to avoid possible damage to the testing machine platens. The threaded portions of the one or more threaded connections in second outer plate 102 and the first outer plate 108 may be based on sufficient load carrying capacity. Additionally, to further support the one or more threaded connections, supplementary support such as one or more nuts may be fastened to the rod in order to add bearing to carry the applied load. In one or more scenarios, the uppermost plate, i.e., the second outer plate 102, which impacts the testing machine platen, is configured to be fastened to four rods that pass through the upper inner plate, i.e., inner plate 104, through holes 202a, 202d, 204a, 204d, and connect to the lower inner plate, i.e., inner plate 106. Inner plate 106 may be connected to the bottom test sample end fixture, such as, the second end fixture 114b. Fasteners may be connected to the respective rods on each side of the inner plate 106 at holes 202a, 202d, 204a, 204d in order to fix the second box at a constant length. Additionally, such a connection allows the size of the second box to be adjusted to the size of different testing machines. The lowermost plate, i.e., the first outer plate 108, is configured to be fastened to four rods that pass through inner plate 106, through holes 202b, 202c, 204b, and 204c, and connect to the upper inner plate, i.e. inner plate 104. Fasteners may be connected to the respective rods on each side of the inner plate 104 at holes 202b, 202c, 204b, and 204c, in a similar manner as described with respect to inner plate 106, in order to fix the first box at a constant length. The inner plate 104 may be connected to the top test sample end fixture, such as, the first end fixture 114a.

A variety of additional aspects will be set forth in the description that follows. The aspects can relate to individual features and to combinations of features. It is to be understood that both the foregoing general description and the following detailed description are exemplary and explanatory only and are not restrictive of the broad inventive concepts upon which the embodiments disclosed herein are based.

BRIEF DESCRIPTION OF THE DRAWINGS

The following drawings are illustrative of particular embodiments of the present disclosure and therefore do not limit the scope of the present disclosure. The drawings are not to scale and are intended for use in conjunction with the explanations in the following detailed description.

FIG. 2A illustrates a top view of an example inner plate.

FIG. 2B illustrates a top view of a first outer plate.

FIG. 2C illustrates a top view of a second outer plate.

DETAILED DESCRIPTION

Figure 1:
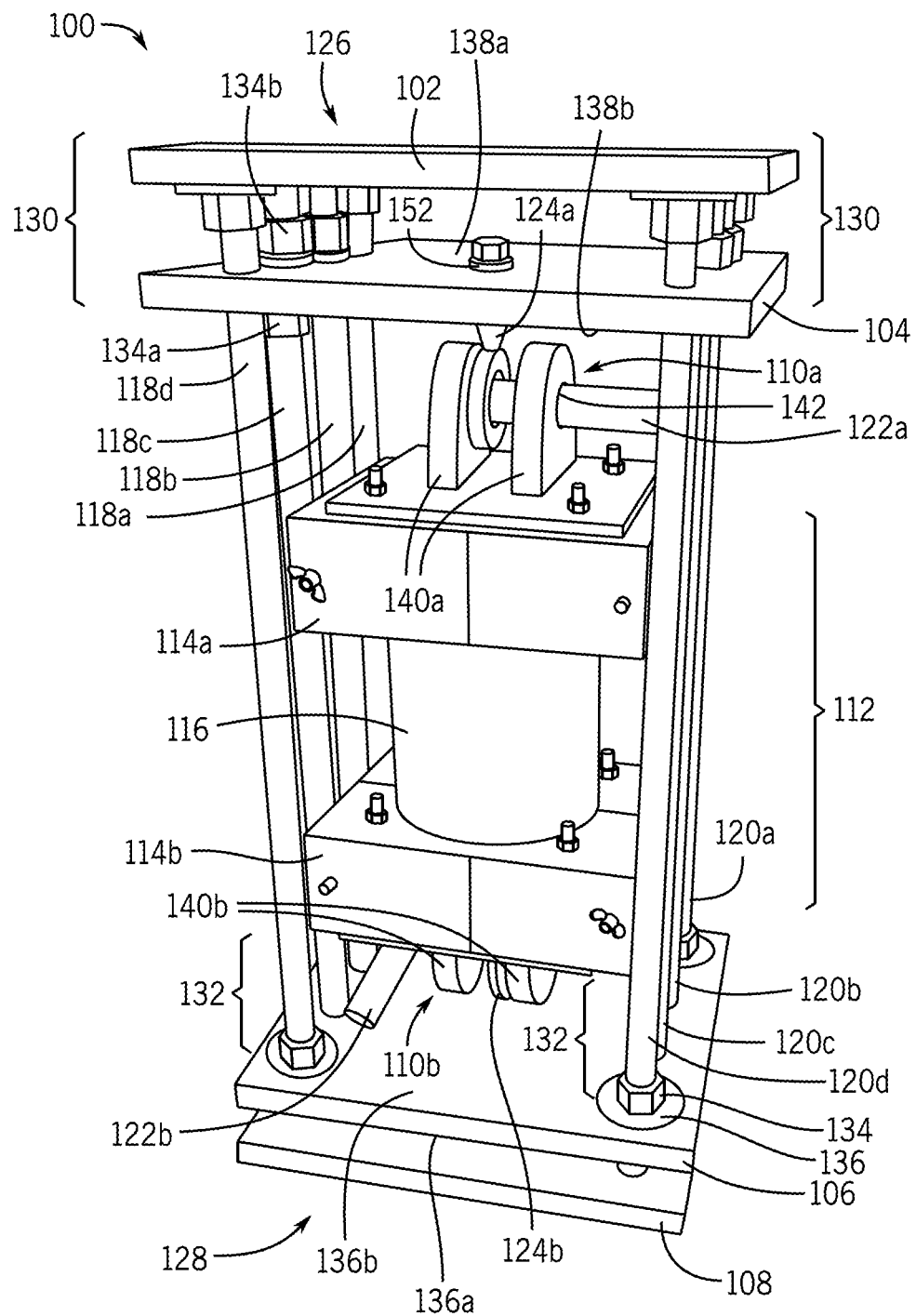
FIG. 1 illustrates an isometric view of an example tension testing apparatus.

The following discussion omits or only briefly describes conventional features of concrete testing methods and concrete testing apparatus, which are apparent to those skilled in the art. It is noted that various embodiments are described in detail with reference to the drawings, in which like reference numerals represent like parts and assemblies throughout the several views. Reference to various embodiments does not limit the scope of the claims attached hereto. Additionally, any examples set forth in this specification are intended to be non-limiting and merely set forth some of the many possible embodiments for the appended claims. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

Embodiments of the present disclosure relate generally to concrete testing methods and a concrete testing apparatus, and more particularly, to a tension testing apparatus. Embodiments of the tension testing apparatus are described below with reference to FIGS. 1-5B.

Figure 4:
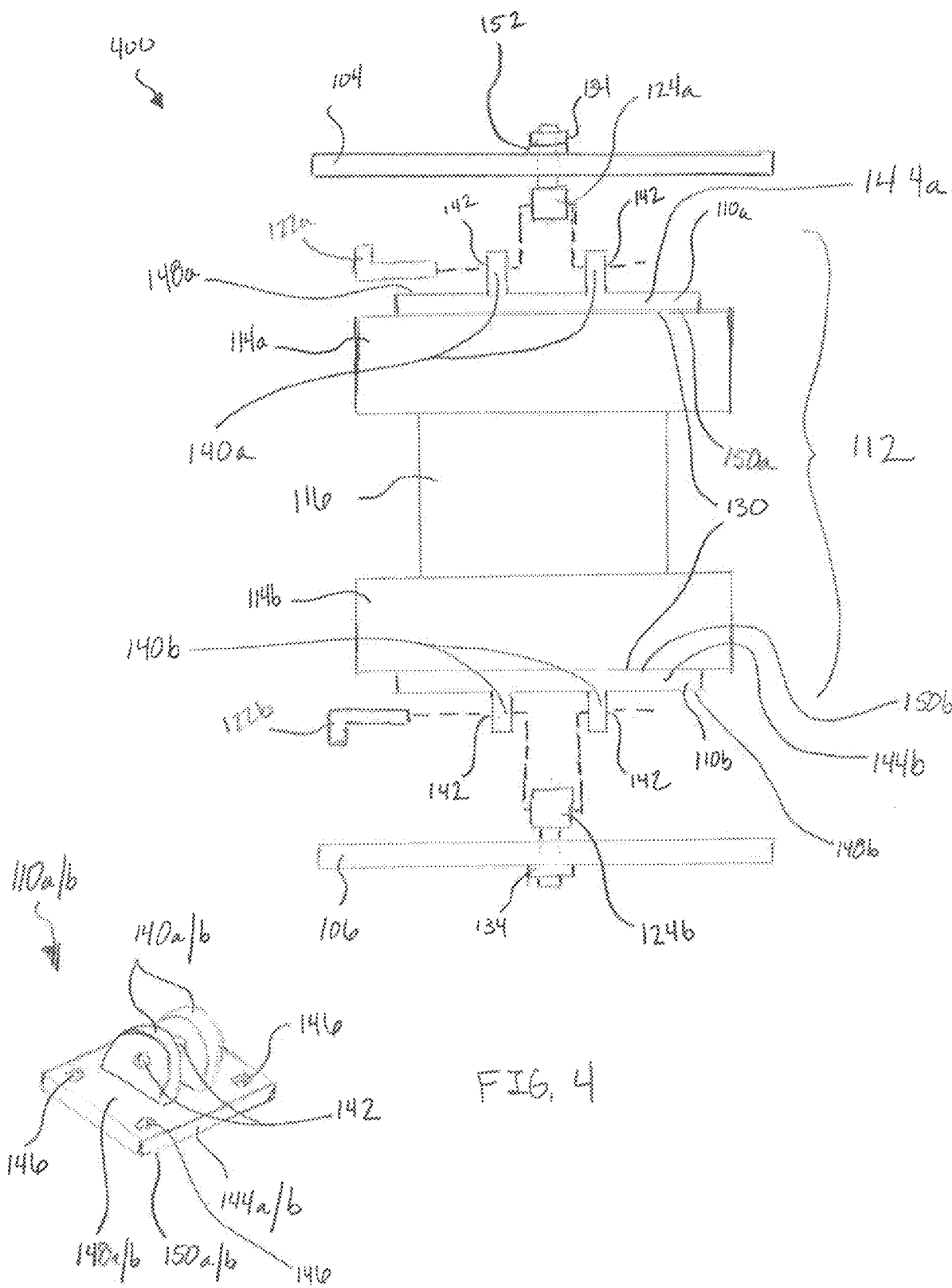
FIG. 4 illustrates an exploded view of a load frame connection.

FIG. 1 illustrates an isometric view of an example tension testing apparatus 100 (hereinafter the "apparatus 100"). FIG. 2A illustrates a top view of an example inner plate, such as inner plate 104 and inner plate 106. FIG. 2B illustrates a top view of a second outer plate 102. FIG. 2C illustrates a top view of a first outer plate 108. FIG. 4 illustrates an exploded view of a load frame connection 400.

The apparatus 100 includes two boxes and a test sample holding system 112 (hereinafter the "system 112") that are interconnected via load frame connectors, such as load frame connector 110a and load frame connector 110b.

The first box of the apparatus 100 includes first outer plate 108 and inner plate 104 connected via one or more rods. A rod may be an elongated rigid member. The rod may be comprised of a metal or an alloy. In one or more cases, the outer circumferential surface of the rod is threaded from one end of the rod to an opposing end of the rod. In one or more other cases, a lower end portion 132 of the rod and an upper end portion 130 of the rod is threaded.

The first outer plate 108 includes a receiving portion for each rod that is used to connect the first outer plate 108 and inner plate 104. For example, if four rods are used to connect the first outer plate 108 and inner plate 104, then the first outer plate 108 includes four receiving portions, such as receiving portions 202g, 202h, 204g, and 204h. A lower end portion 132 of a rod is disposed towards the lower end 128 of the apparatus 100. The lower end portion 132 of the rod may couple to a receiving portion of the first outer plate 108. For example, a lower end portion 132 of rod 118b couples to receiving portion 202g, a lower end portion 132 of rod 118c couples to receiving portion 202h, a lower end portion 132 of rod 120b couples to receiving portion 204g, and a lower end portion 132 of rod 120c couples to receiving portion 204h.

In one or more cases, a receiving portion of the first outer plate 108 may be threaded. A lower end portion 132 of a rod may be threaded to correspond to the threaded portion of the receiving portion of the first outer plate 108. The lower end portion 132 of a rod may be coupled to the receiving portion by fastening the threaded end of the lower end portion 132 with the threaded portion of the receiving portion. To further secure the rod to the first outer plate 108, the rod may be inserted through a washer 136 and a fastener 134, such as a nut or type of nut such as a wing nut, and into the receiving portion of the first outer plate 108. Having coupled the lower end portion 132 of the rod to the receiving portion, the fastener 134 may be used to tighten the rod to the receiving portion. For example, a user may rotate a nut around the rod such that the nut tightens the rod to the receiving portion.

The inner plate 104 includes a receiving portion for each rod that is used to connect the first outer plate 108 and inner plate 104. For example, the inner plate 104 includes four receiving portions, such as receiving portions 202b, 202c, 204b, and 204c. An upper end portion 130 of the rod is disposed towards the upper end 126 of the apparatus 100. The upper end portion 130 of the rod may couple to a receiving portion of the inner plate 104. For example, an upper end portion 130 of rod 118b couples to receiving portion 202b, an upper end portion 130 of rod 118c couples to receiving portion 202c, an upper end portion 130 of rod 120b couples to receiving portion 204b, and an upper end portion 130 of rod 120c couples to receiving portion 204c. In one or more cases, receiving portions 202b, 202c, 204b, and 204c may be through holes, in which each through hole is configured to allow at least a portion of a rod to pass through the inner plate 104 and the inner plate 106. In one or more cases, to couple the upper end portion 130 of a rod, for example, rod 118b, 118c, 120b, and 120c, to the inner plate 104, a washer and fastener 134a are positioned on the rod on an inner surface side 138b of the inner plate 104, the rod is inserted through the receiving portion, and another washer and fastener 134b are positioned on the rod on an outer surface side 138a of the inner plate 104. In one or more other cases, the washer and fastener are positioned on the rod on the outer surface side 138a of the inner plate 104, the rod is inserted through the receiving portion, and the other washer and fastener are positioned on the rod on an inner surface side 138b of the inner plate 104. The fastener 134a on the inner surface side 138b and the fastener 134b on the outer surface side 138b are fastened towards one another, thereby coupling the upper end portion 130 of the rod to the inner plate 104.

The second box of the apparatus 100 includes a second outer plate 102 and inner plate 106 connected via the one or more rods used to connect the components of the first box.

The second outer plate 102 includes a receiving portion for each rod that is used to connect the second outer plate 102 and the inner plate 106. For example, if four rods are used to connect the second outer plate 102 and the inner plate 106, then the second outer plate 102 includes four receiving portions, such as receiving portions 202e, 202f, 204e, and 204f. An upper end portion 130 of a rod is disposed towards the upper end 126 of the apparatus 100. The upper end portion 130 of the rod may couple to a receiving portion of the second outer plate 102. For example, an upper end portion 130 of rod 118a couples to receiving portion 202e, an upper end portion 130 of rod 118d couples to receiving portion 202f, an upper end portion 130 of rod 120a couples to receiving portion 204e, and an upper end portion 130 of rod 120d couples to receiving portion 204f.

In one or more cases, a receiving portion of the second outer plate 102 may be threaded. An upper end portion 130 of a rod may be threaded to correspond to the threaded portion of the receiving portion of the second outer plate 102. The upper end portion 130 of a rod may be coupled to the receiving portion by fastening the threaded end of the upper end portion 130 with the threaded portion of the receiving portion. To further secure the rod to the second outer plate 102, the rod may be inserted through a washer, such as washer 136, and a fastener, such as fastener 134, and into the receiving portion of the second outer plate 102. Having coupled the upper end portion 130 of the rod to the receiving portion, the fastener may be used to tighten the rod to the receiving portion. For example, a user may rotate the fastener around the rod such that the fastener tightens the rod to the receiving portion.

The inner plate 106 includes a receiving portion for each rod that is used to connect the second outer plate 102 and inner plate 106. For example, the inner plate 106 includes four receiving portions, such as receiving portions 202a, 202d, 204a, and 204d. A lower end portion 132 of the rod is disposed towards the lower end 128 of the apparatus 100. The lower end portion 132 of the rod may couple to a receiving portion of the inner plate 106. For example, a lower end portion 132 of rod 118a couples to receiving portion 202a, a lower end portion 132 of rod 118d couples to receiving portion 202d, a lower end portion 132 of rod 120a couples to receiving portion 204a, and a lower end portion 132 of rod 120d couples to receiving portion 204d. In one or more cases, receiving portions 202a, 202d, 204a, and 204d may be through holes, in which each through hole is configured to allow at least a portion of a rod to pass through the inner plate 104 and the inner plate 106. In one or more cases, to couple the lower end portion 132 of a rod, for example, rod 118a, 118d, 120a, and 120d, to the inner plate 106, a washer and a fastener, such as washer 136 and fastener 134, are positioned on the rod on an inner surface side 136b of the inner plate 106, the rod is inserted through the receiving portion, and another washer and fastener, such as washer 136 and fastener 134, are positioned on the rod on an outer surface side 136a of the inner plate 106. In one or more other cases, the washer and fastener are positioned on the rod on the outer surface side 136a, the rod is inserted through the receiving portion, and the other washer and fastener are positioned on the rod on the inner surface side 136b. The fastener on the inner surface side 136b and the fastener on the outer surface side 136a are fastened towards one another, thereby coupling the lower end portion 132 of the rod to the inner plate 106.

The receiving portions of the second outer plate 102, the inner plate 104, the inner plate 106, and the first outer plate 108 may be aligned with one another. For example, receiving portion 202e of the second outer plate 102 may be aligned with the receiving portion 202a of the inner plate 104 and the receiving portion 202a of the inner plate 106, in which rod 118a can be attached to the second outer plate 102, pass through the receiving portion 202a of the inner plate 104, and attached to the receiving portion 202a of the inner plate 106. In another example, receiving portion 202g of the first outer plate 108 may be aligned with the receiving portion 202b of the inner plate 104 and the receiving portion 202b of the inner plate 106, in which rod 118b can be attached to the first outer plate 108, pass through the receiving portion 202b of the inner plate 106, and attached to the receiving portion 202b of the inner plate 104. The receiving portions may be linearly arranged on the respective plate. For example, receiving portions 202a, 202b, 202c, and 202d may be linearly arranged with one another in a longitudinal direction of the inner plate, and receiving portions 202a and 204a may be linearly arranged with one another in a lateral direction of the inner plate.

The system 112 includes a first end fixture 114a and a second end fixture 114b configured to hold a test sample 116. The system 112 may be removably coupled to the first box and the second box, via a first load frame connector 110a and a second load frame connector 110b, respectively. The first load frame connector 110a is removably coupled to the first end fixture 114a, via one or more fasteners, and to the inner plate 104, via a pin and bolt configuration. The second load frame connector 110b is removably coupled to the second end fixture 114b, via one or more fasteners, and to the inner plate 106, via another pin and bolt configuration. A bolt, such as bolt 124a and 124b, may be an eye bolt coupled to a respective inner plate, in which the loop end of the eye bolt is positioned on the inner surface side of the respective inner plate and the opposing end of the eye bolt is fastened to the outer surface side of the respective inner plate, via fastener 134. For example, bolt 124a may be coupled to inner plate 104, in which the loop end of the bolt 124a is positioned on the inner surface side 138b of the inner plate 104 and the opposing end of the bolt 124a is fastened to the outer surface side 138a of the inner plate 104 via fastener 134. In one or more cases, a bolt load cell 152 or a like measuring device is positioned on a portion of the bolt 124a that is located on the outer side surface 138a of the inner plate 104, and fastener 134 may be positioned on top of the bolt load cell 152. The bolt load cell 152 may be used as a load cell in-flight on the tension testing apparatus 100, thereby eliminating any stiffness and/or load effects that may deflect the testing machine itself during loading. By positioning the bolt load cell 152 on the bolt 124a as a load cell in-flight, the bolt load cell 152 can provide a direct measurement of the tension force applied to the test sample 116. In one or more other cases, the bolt load cell 152 or a like measuring device is positioned on a portion of the bolt 124*b* that is located on the outer side surface 136*a* of the inner plate 106, and fastener 134 may be positioned on top of the bolt load cell 152.

The load frame connector includes a transfer plate, such as transfer plate 144*a* and 144*b*, in which at least one rigid connection members, such as connection members 140*a* and 140*b*, protrude from an upper surface, such as upper surface 148*a* and 148*b*, of the transfer plate. Each of the connection members includes a through hole 142, which is configured to receive a rod, such as rod 122*a* and 122*b*. The load frame connector includes one or more through holes 146, in which a fastener may be inserted through the through holes 146 and fastened to a receiving portion 312 on an outer surface 318 of an end fixture. The load frame connector may be positioned on the outer surface 130. The lower surface, such as lower surface 150*a* and 150*b*, may contact the upper outer surface 130 of the end fixture. Having fastened the load frame connector to a respective end fixture, the rod may be inserted through each through hole 142 of the respective connection member and though the bolt. For example, rod 122*a* may be inserted through each through hole 142 of connection member 140*a* and through the bolt 124*a*, thereby coupling the first end fixture 114*a* to the inner plate 104, via the first load frame connector 110*a*. In some cases, the rod may be configured to receive a pin in order to secure the rod to the load frame connector. For example, the pin may be a cotter pin, split pin, or another type of pin known to one of ordinary skill in the art.

Figure 3A:
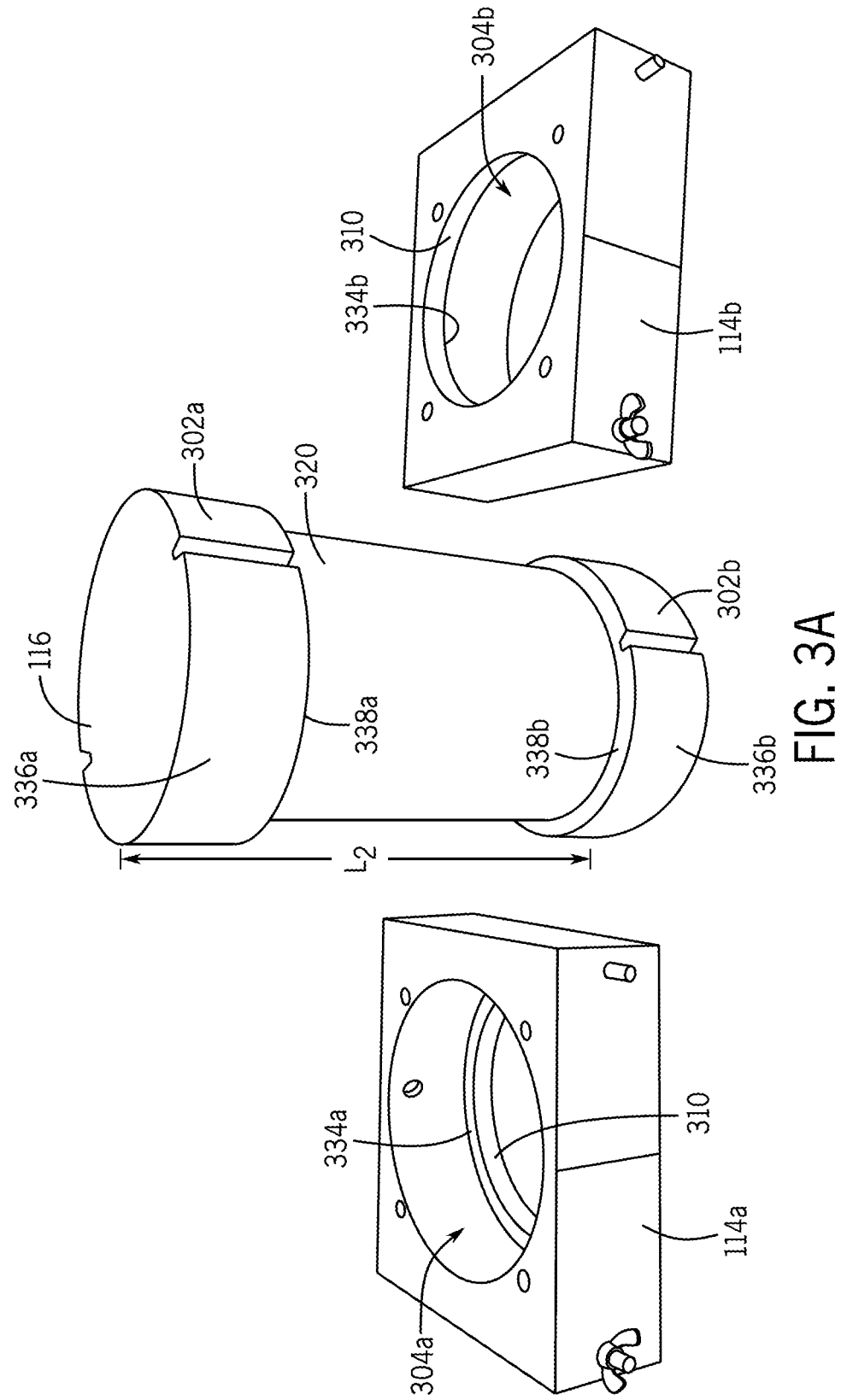
FIG. 3A illustrates an unassembled view of a test sample clamping system.
Figure 3B:
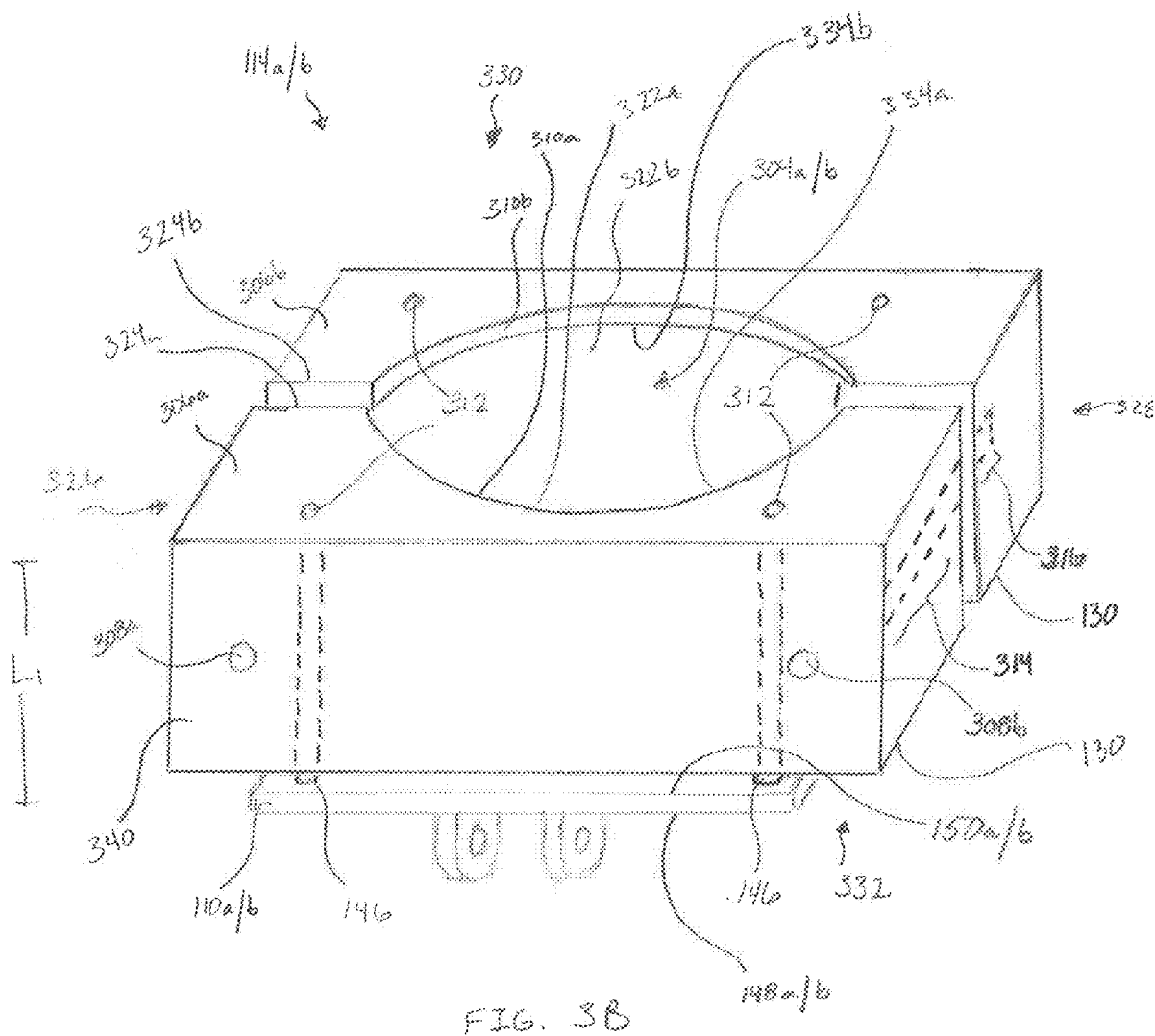
FIG. 3B illustrates an isometric view of an end fixture of the test sample clamping system of FIG. 3A.
Figure 3C:
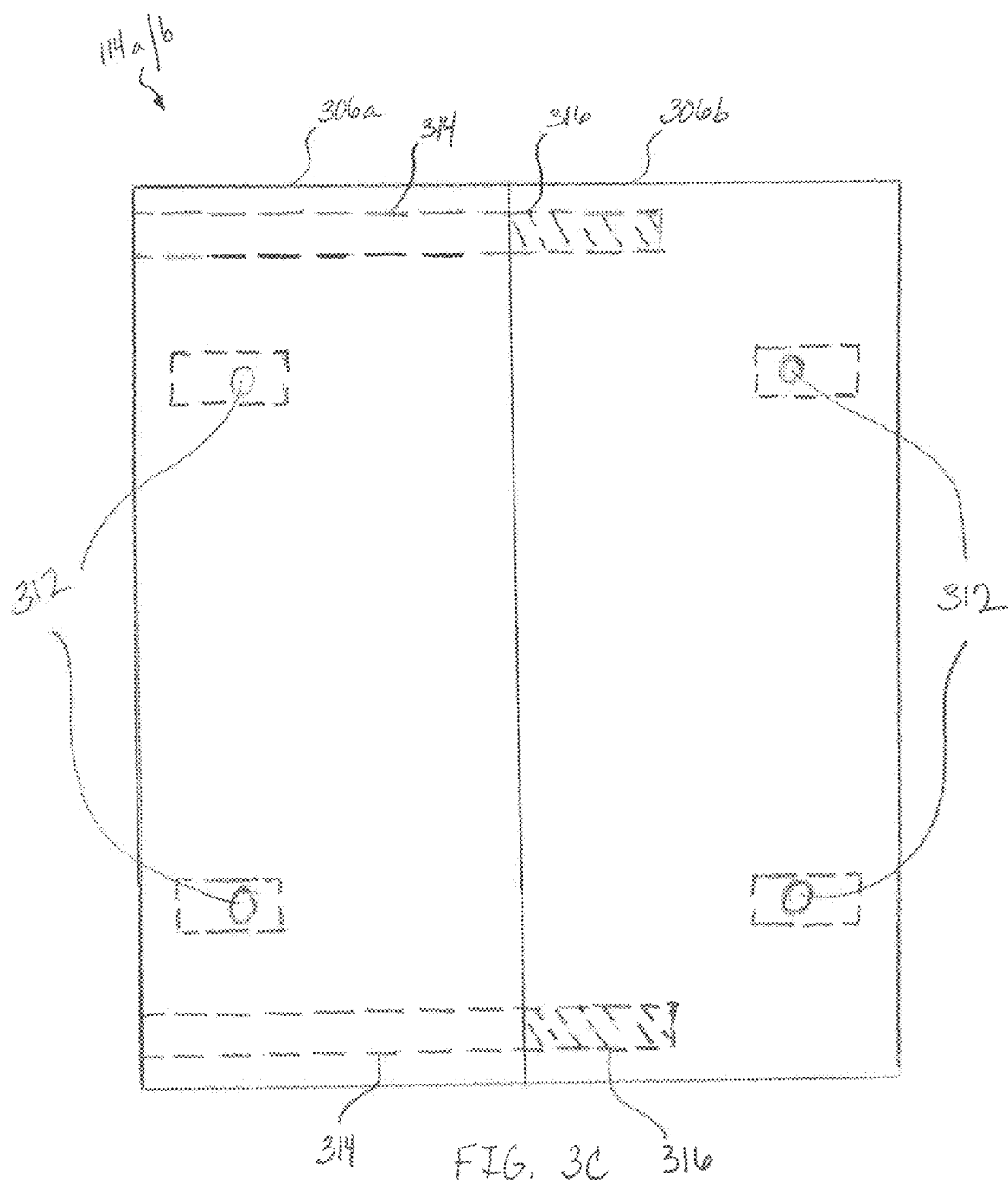
FIG. 3C illustrates a bottom view of the end fixture of the test sample clamping system of FIG. 3A.

FIG. 3A illustrates an unassembled view of the system 112. FIG. 3B illustrates an isometric view of an end fixture of the system 112 of FIG. 3A. FIG. 3C illustrates a bottom view of the end fixture of the system 112 of FIG. 3A.

The test sample 116 may be concrete solidified in a cylindrical shape. A test sample cover, such as test sample cover 302*a* and test sample cover 302*b*, may be coupled to each end of the test sample 116. For example, the test sample cover 302*a* is attached around the outer cylindrical surface 320 on one end of the test sample 116, via adhesive, and the test sample cover 302*b* is attached around the outer cylindrical surface 320 on an opposing end of the test sample 116, via adhesive. The first end fixture 114*a* is positioned around the test sample cover 302*a*. The second end fixture 114*b* is positioned around the test sample cover 302*b*. In one or more cases, the length $L_1$ of the first end fixture 114*a* and the second end fixture 114*b* may be at or about ¼ the length $L_2$ of the test sample 116, in which "about" ranges+/−20% of the ¼ the length $L_2$ of the test sample 116.

The first end fixture 114*a* includes two halved portions (FIG. 3B), such as a first portion 306*a* and a second portion 306*b*. Similarly, the second end fixture 114*b* includes two portions. The second end fixture 114*b* includes one or more features of the first end fixture 114*a*. Accordingly, the description herein discusses features of the first end fixture 114*a*, and to avoid repetition, a redundant description of one or more of these features with respect to the second end fixture 114*b* is not included. It is noted that like drawing reference numbers include the like features. For example, the features of the test sample cover 302*a* are equally applicable to the features of the test sample cover 302*b*.

The first portion 306*a* includes a curved area 322*a* located on a proximal side 324*a* of the first portion 306*a*. The curved area 322*a* may be configured in a shape of the test sample 116 in order to surround at least a portion of the test sample 116. The radius of the curved area 322*a* may correspond to the radius of the test sample cover 302*a*. In one or more cases, the curved area 322*a* may be formed such that the curved area 322*a* contacts the test sample cover 302*a*. The curved area 322*a* includes a bearing rim 310*a* positioned on a lower area 330 of the first portion 306*a*. The radius of the bearing rim 310*a* may be smaller than the radius of the curved area 322*a*. The radius of the bearing rim 310*a* may correspond to the radius of the outer cylindrical surface 320 of the test sample 116. The inner surface 334*a* of the bearing rim 310*a* is configured to contact the surface 338*a* of the test sample cover 302*a*, in which the surface 338*a* is perpendicular to the outer circumferential surface 336*a* of the test sample cover 302*a*.

The second portion 306*b* includes a curved area 322*b* located on a proximal side 324*b* of the second portion 306*b*. The curved area 322*b* may be configured in a shape of the test sample 116 in order to surround at least a portion of the test sample 116. The radius of the curved area 322*b* may correspond to the radius of the test sample cover 302*a*. In one or more cases, the curved area 322*b* may be formed such that the curved area 322*b* contacts the test sample cover 302*a*. The curved area 322*b* includes a bearing rim 310*b* positioned on a lower area 330 of the second portion 306*b*. The radius of the bearing rim 310*b* may be smaller than the radius of the curved area 322*b*. The radius of the bearing rim 310*b* may correspond to the radius of the outer cylindrical surface 320 of the test sample 116. The inner surface 334*b* of the bearing rim 310 is configured to contact the surface 338*b* of the test sample cover 302*a*, in which the surface 338*b* is perpendicular to the outer circumferential surface 336*a* of the test sample cover 302*a*.

The first portion 306*a* and the second portion 306*b* are configured to be coupled together forming a test sample receiving portion. The test sample receiving portion 304*a* is configured to house the test sample 116 and the test sample cover 302*a*. The test sample receiving portion 304*b* is configured house the test sample 116 and the test sample cover 302*b*. The first portion 306*a* and the second portion 306*b* may be coupled around the test sample 116 and a test sample cover, such as test sample cover 302*a* and test sample cover 302*b*.

In one or more cases, the first portion 306*a* includes a through hole 314, and the second portion 306*b* includes a threaded portion 316. The first portion 306*a* includes a receiving portion, such as receiving portion 308*a* and 308*b*, on a vertical surface 340 of the first portion 306*a*, in which the receiving portion defines an outer end of the through hole 314. A fastener, for example a bolt having a threaded end, may be inserted through a receiving portion, such as receiving portion 308*b*, and through hole 314 and into the threaded portion 316. The fastener may include a threaded portion on the proximal end of the fastener, in which the threaded portion corresponds to the threaded portion 316. Having positioned the first portion 306*a* and second portion 306*b* around the test sample cover 302*a*, the fastener may be tightened to the threaded portion 316, thereby coupling the first end fixture 114*a* to the test sample 116. It should be noted that the second portion 306*b* may include the through hole 314, and the first portion 306*a* may include the threaded portion 316, such that the fastener is inserted into the second portion 306*b* and fastened to the threaded portion 316 in the first portion 306*a*.

In one or more other cases, the first portion 306*a* and the second portion 306*b* each include a through hole, in which each through hole is aligned such that a rod may be inserted into the first portion 306*a* and the second portion 306*b*. The rod may be long enough such that a portion of the rod on each end extends beyond the outer surfaces of the first portion 306*a* and the second portion 306*b*. A washer and fastener, such as fastener 134, may be positioned on each portion of the rod that extends beyond the outer surfaces of the first portion 306a and the second portion 306b. The fasteners on each end of the rod may be tightened such that the first portion 306a and the second portion 306b are coupled together, thereby coupling the first end fixture 114a to the test sample 116.

Figure 5A:
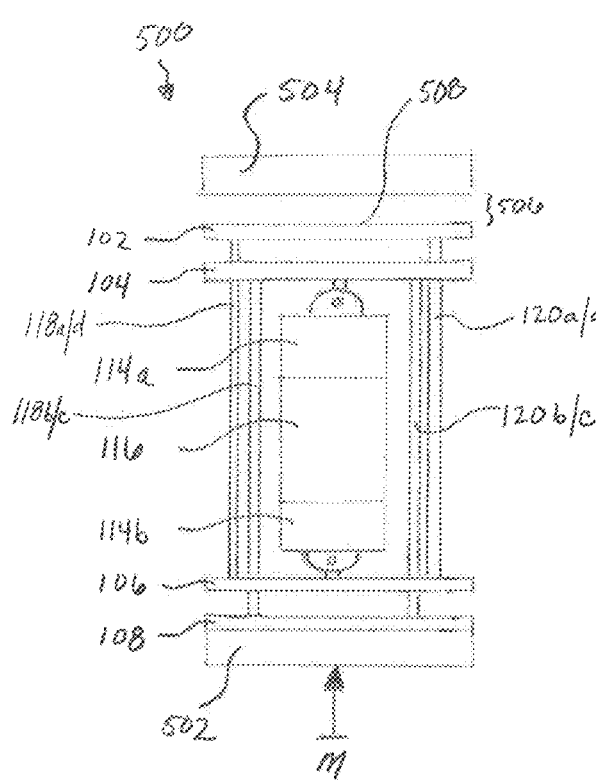
FIG. 5A illustrates loading the example tension testing apparatus in a test machine.
Figure 5B:
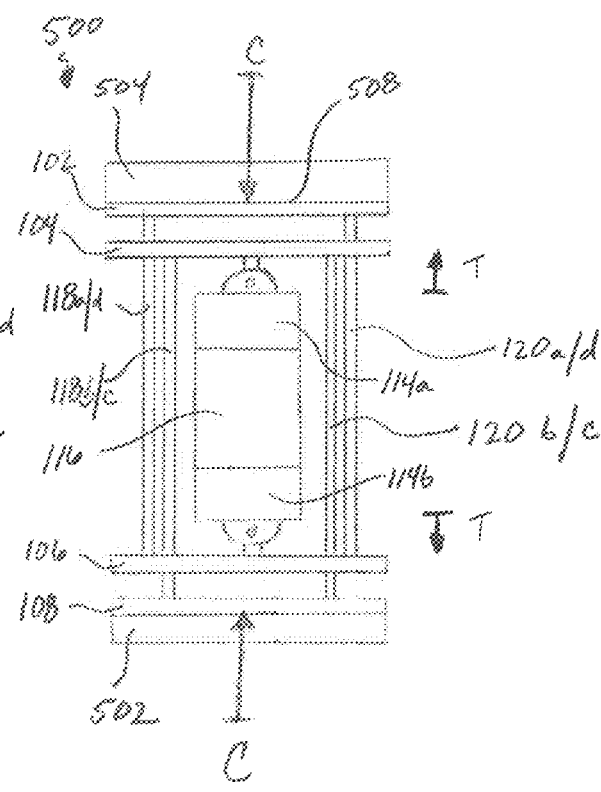
FIG. 5B illustrates applying tension to a test sample in the tension testing apparatus.

FIG. 5A illustrates loading the apparatus 100 in a test machine 500. FIG. 5B illustrates applying tension to a test sample 116 in the apparatus 100.

The test machine 500 includes a test machine moving head 502 and a test machine fixed head 504. In one or more cases, the test machine 500 may be a compression test machine configured to apply compression force to a test sample. The apparatus 100 with the test sample 116 is loaded onto the test machine moving head 502. The test machine moving head 502 closes the gap 506 between the test machine fixing head 504 and the second outer plate 102 by moving the test machine moving head 502 in a direction M towards the test machine fixed head 504. Having closed the gap 506, the test machine moving head 502 contacts an outer surface 508 of the second outer plate 102. As the test machine moving head 502 moves in the direction M, the test machine 500 applies a compression force C to the first box and the second box. As the compression force C moves the first box through the second box, the apparatus 100 applies a tension force T to the test sample 116.

The direct tension loading testing data may be calculated as follows. In a non-limiting example, the test sample 116 may be a concrete specimen having a diameter of 4 in. and an area of 12.56 in.$^2$. The bolt load cell 152 may provide a load reading of 2890 pounds. The stress of the test sample 116 may be 230 psi, which may be calculated by dividing the load reading by the area of the cylinder (e.g., 2890 lbs./12.56 in.$^2$=230 psi). The tension strength of the test sample 116 may be equivalent to the maximum load measured at failure, e.g., 230 psi.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A tension testing apparatus, the apparatus comprising:
a first box comprising a first outer plate and a first inner plate, the first outer plate and the first inner plate being coupled together by at least two rods;
a second box comprising a second outer plate and a second inner plate, the second outer plate and the second inner plate being coupled together by at least two other rods; and
a test sample holding system coupled to the first inner plate and the second inner plate, the test sample holding system being configured to hold a test sample,
wherein the at least two rods of the first box are configured to pass through the second inner plate, and the at least two rods of the second box are configured to pass through the first inner plate;
wherein the test sample holding system is coupled to the first inner plate via a first load frame connector, and is coupled to the second inner plate via a second load frame connector; and
wherein each of the first load frame connector and the second load frame connector comprise a transfer plate and at least one connection member, the at least one connection member protruding from an upper surface of the transfer plate.

2. The apparatus of claim 1, wherein as the at least two rods of the first box passes through the second inner plate, a tension force is applied to the test sample holding system holding a test sample.

3. The apparatus of claim 1, wherein as the first inner plate moves along the at least two other rods of the second box and the second inner plate moves along the at least two rods of the first box, a tension force is applied to the test sample holding system holding a test sample.

4. The apparatus of claim 1, wherein the apparatus is configured to be positioned within a compression testing machine, and wherein as the compression testing machine applies a compression force to an outer surface of the first outer plate and an outer surface of the second outer plate, the apparatus applies a tension force to a first outer end and a second outer end of the test sample.

5. The apparatus of claim 1, wherein a first eye bolt is coupled to a lower surface of the first inner plate and a second eye bolt is coupled to an upper surface of the second inner plate, and wherein the at least one connection member of the first load frame connector is coupled to the first eye bolt and the at least one connection member of the second load frame connector is coupled to the second eye bolt.

6. The apparatus of claim 1, wherein the test sample holding system is configured to hold the test sample via a first end fixture and a second end fixture, and wherein the first end fixture and the second end fixture are positioned at opposing ends of the test sample in a lengthwise direction, and wherein the first end fixture and the second end fixture are each positioned around an outer surface of the test sample.

7. The apparatus of claim 1, wherein test sample holding system is configured to hold the test sample via an end fixture positioned at an end of the test sample.

8. The apparatus of claim 7, wherein the test sample holding system is coupled to a first inner plate via a load frame connector, and wherein a transfer plate of the load frame connector is coupled to the end fixture.

9. The apparatus of claim 7, wherein the end fixture comprises two portions configured to be coupled to one another around an outer surface of the test sample.

10. The apparatus of claim 9, wherein each of the two portions includes a housing portion configured in a shape of the outer surface of the test sample, and wherein the housing portion is configured to surround at least a portion of the outer surface.

11. The apparatus of claim 9, wherein a test sample cover is coupled to an end of the test sample, wherein each of the two portions includes a bearing rim configured to contact an inner surface of the test sample cover, the inner surface of the test sample cover being perpendicular to the outer surface of the test sample.

12. The apparatus of claim 7, wherein a length of the end fixture is at or about ¼ the length of the test sample.

13. A tension testing system, the system comprising:
a testing machine configured to apply compression force to a test sample, the testing machine comprising a moving head and a fixed head; and
a tension testing apparatus configured to be positioned within the testing machine, the tension testing apparatus comprising:
a first box comprising a first outer plate and a first inner plate, the first outer plate and the first inner plate being coupled together by at least two rods, a second box comprising a second outer plate and a second inner plate, the second outer plate and the second inner plate being coupled together by at least two other rods, and a test sample holding system coupled to the first inner plate and the second inner plate, the test sample holding system being configured to hold a test sample;

wherein the at least two rods of the first box are configured to pass through the second inner plate, and the at least two rods of the second box are configured to pass through the first inner plate;

wherein the test sample holding system is coupled to the first inner plate via a first load frame connector, and is coupled to the second inner plate via a second load frame connector; and wherein each of the first load frame connector and the second load frame connector comprise a transfer plate and at least one connection member, the at least one connection member protruding from an upper surface of the transfer plate.

14. The system of claim 13, wherein as the testing machine applies a compression force to an outer surface of the first outer plate and an outer surface of the second outer plate, the tension testing apparatus applies a tension force to a first outer end and a second outer end of the test sample.

15. The system of claim 13, wherein the moving head is configured to apply a compression force to an outer surface of the first outer plate, and wherein the moving head is configured to apply a compression force to an outer surface of the second outer plate.

\* \* \* \* \*